United States Patent
Boschetti et al.

(10) Patent No.: US 7,312,327 B2
(45) Date of Patent: Dec. 25, 2007

(54) METHOD OF PREPARING NITROGEN MACROCYCLES

(75) Inventors: Frederic Boschetti, Dijon (FR); Franck Denat, Dijon (FR); Roger Guilard, Fontaine les Dijon (FR); Henry Ledon, Versailles (FR); Herve Chollet, Dijon (FR); Jean-Louis Babouhot, Fontaine les Dijon (FR)

(73) Assignees: Centre National de la Recherche Scientifique (C.N.R.S.), Paris (FR); Commissariat a l'energie Atomique, Paris (FR)

( * ) Notice: Subject to any disclaimer, the term of this patent is extended or adjusted under 35 U.S.C. 154(b) by 309 days.

(21) Appl. No.: 10/490,948

(22) PCT Filed: Sep. 27, 2002

(86) PCT No.: PCT/FR02/03319

§ 371 (c)(1),
(2), (4) Date: Mar. 26, 2004

(87) PCT Pub. No.: WO03/029228

PCT Pub. Date: Apr. 10, 2003

(65) Prior Publication Data

US 2004/0206940 A1    Oct. 21, 2004

(30) Foreign Application Priority Data

Sep. 28, 2001    (FR) .................................. 01 12550

(51) Int. Cl.
*C07D 257/02*    (2006.01)
(52) U.S. Cl. .................................................... 540/474
(58) Field of Classification Search ................. 540/474
See application file for complete search history.

(56) References Cited

U.S. PATENT DOCUMENTS 5,417,960 A * 5/1995 Schaefer et al. ......... 424/9.363

FOREIGN PATENT DOCUMENTS

| WO | WO 00/21941 | 4/2000 |
| WO | WO 00/32581 | 6/2000 |
| WO | WO 00/32601 | 6/2000 |
| WO | WO 00/53588 | 9/2000 |

OTHER PUBLICATIONS

Weisman G R et al: "Cross-Bridged Cyclam. Protonation and LI+ Complexation in a Diamond-Lattice Cleft" Journal of the American Chemical Society, American Chemical Society, Washington, DC, US, vol. 112, No. 23, 1990, pp. 8604-8605, XP002066456.

Weisman G R et al: "Tetracyclic Tetraamines by Glyoxal-Macrocyclic Tetraamine Condensation" Tetrahedron Letter, Elsevier Science Publishers, Amsterdam, NL, vol. 21, 1980, pp. 335-338, XP002002301.

P. Tundo: "Alkyl substituted tetraaza-cycloalkanes: carriers of transition metal ions in organic phase and catalysts of anion promoted reactions" Tetrahedron Letters, No. 47, 1978, pp. 4693-4696, XP002200093.

* cited by examiner

*Primary Examiner*—Brenda Coleman
(74) *Attorney, Agent, or Firm*—Young & Thompson

(57) ABSTRACT

The invention relates to a method of preparing nitrogen macrocycles having formula (I). The inventive method comprises a step involving the reaction of compounds (II) and (III) in order to form a compound having formula (IV). Said compound is subsequently made to react with a compound having formula (V) in order to form a compound having formula (VI). The latter compound is then subjected to an acid treatment 3 Claims, 3 Drawing Sheets Scheme 1 (PRIOR ART)

Scheme 2 (PRIOR ART)

Scheme 3 (PRIOR ART)

Scheme 4 (PRIOR ART)

Scheme 5

METHOD OF PREPARING NITROGEN MACROCYCLES

This application is a national stage entry under 35 USC §371 of PCT/FR02/03319, filed Sep. 27, 2002.

BACKGROUND OF THE INVENTION

The chemistry of cyclic polyamines, and in particular of tetraazacycloalkanes, the two main representatives of which are 1,4,7,10-tetraazacyclododecane (cyclen) and 1,4,8,11-tetraazacyclotetradecane (cyclam), has expanded considerably. The derivatives of these polyazamacrocycles find applications in fields as diverse as the purification of liquids, catalysis or medicine. Cyclen is, for example, the base unit of numerous contrast agents in medical imaging. The N-functionalization of these macrocycles and the study of the complexing properties of the novel ligands thus obtained have formed the subject of numerous studies.

The selectivity of the macrocycle with respect to a given substrate depends on the nature, on the number and on the relative position of the chelating arms. Most applications require the fixing of the macrocycles, either to a solid support or to an antibody. The synthesis of molecules comprising both a complexing site, such as a nitrogenous macrocycle carrying suitable chelating arms, and a reactive ending which makes possible grafting to an antibody or to a solid support has formed the subject of numerous publications and patent applications over the last decade. However, such bifunctional chelating agents (BCA or BFC) are difficult to prepare, in particular when different functional groups have to be condensed to the nitrogen atoms of the ring.

Numerous relatively selective methods for the N-functionalization of tetraazacycloalkanes have been described. In point of fact, most of them require either the use of a large excess of the base macrocycle, still relatively expensive, or the tedious implementation of successive sequences of protection and of deprotection of reaction sites.

Another approach consists in introducing the arm which makes possible the grafting onto a carbon atom of the macrocycle backbone and then the chelating arms onto the nitrogen atoms. The latter approach appears better suited to the synthesis of these bifunctional chelating agents as it makes it possible, on the one hand, to retain the four secondary amine functional groups without detrimentally affecting the properties of the macrocycle and, on the other hand, to easily attach four chelating arms during a stage of complete N-functionalization. This approach has been applied in the synthesis of numerous bifunctional chelating agents, some of which, represented in FIG. 1, are used in clinical trials on human beings and/or are available commercially (BAT, p-NCS-Bz-DOTA, p-$NH_2$-Bz-DOTA). However, it remains limited by the problematic synthesis of the C-functionalized macrocycles.

This is because a synthesis by formation of a C-C bond to the macrocycle cannot be envisaged. It necessarily involves the use of a synthon carrying the desired functional group or an intermediate which makes possible access to the latter. Several cyclization methods have been developed. None is general and allows access without distinction to the cyclam, to the cyclen or to other macrocycles.

In the case of cyclam derivatives, the most widely used method to date is that of Tabushi et al., represented by scheme 1, based on the condensation of a linear tetraamine with a functionalized diethyl malonate[1]. This is because the acidity of the hydrogen atoms of the methylene group makes possible easy functionalization of the diester. The diamide obtained is subsequently reduced to result in the C-functionalized cyclam. Numerous cyclams C-substituted at the carbon atom in the 6 position have been synthesized by this route[2-11]. This approach has also been made possible the production of biscyclams connected via carbon atoms[12-14] and the synthesis of C-functionalized 1,4,7,10-tetraazatridecanes (2223)[3,15,16]. Finally, the anchoring of cyclic tetraamines to organic polymers has been carried out according to this reaction scheme[17,18]. The main advantage of this method is the possibility of introducing highly varied functional groups onto the macrocycle. However, it exhibits numerous disadvantages: it cannot be applied to the cyclen series, it requires a stage of reduction of the intermediate diamide carried out with a large excess of borane, and the reaction times are long, up to 20 days for the cyclization stage. Furthermore, the reaction yields remain low despite the optimization of the cyclization conditions[19, 20].

Another method, represented by scheme 2, which consists of the Michael addition of a linear tetraamine to a coumarin or to an ethyl acrylate derivative and then a reduction with borane of the cyclic amide obtained, has made possible the production of cyclams C-functionalized in the 5 position by a phenol, nitrophenol[21,22], pyridine[23], imidazole[24], hydroxypyridine[25] or triphenylphosphine[26] group. The disadvantages of this method are the same as those of the method of Tabushi et al.; the cyclization stage lasts three weeks at reflux in ethanol, the yield of the cyclization is low (8 to 40%) and it is subsequently necessary to reduce the intermediate amide.

The synthesis of 4-nitrobenzyl-cyclen (p-$NO_2$-Bn-cyclen), a precursor of 2-(4-nitrobenzyl)-1,4,7,10-tetrakis (carboxymethyl)-cyclen (p-$NH_2$-Bn-DOTA), has formed the subject of several publications and patent applications[5,27-30]. The synthesis represented by scheme 3 involves synthons N-substituted by groups of tosyl type and is directly inspired by the method of producing cyclen according to Richman and Atkins[31].

Other C-functionalized cyclens have also been obtained by this method [32-36]. While the cyclization yields are generally good, the disadvantages of the method of Richman and Atkins are reencountered here, the drastic detosylation conditions, the sulfonamide intermediates and the not very economic aspect in terms of atoms involved (non atom economic), to which is to be further added the difficulty of obtaining the C-functionalized synthons. This approach has also been used for the synthesis of cyclams functionalized in the 6[37,38] or 5[39] positions or of larger C-substituted tetraaza-cyclo-alkanes[37,38,40].

Another access route to macrocycles consists in using an external support, generally a metal cation, to bring the synthons into a conformation favorable to the cyclization reaction. A "template effect" is then referred to. This approach, which makes possible an effective synthesis of the cyclam[41,42], has also been proposed for the production of C-functionalized macrocycles. The most widely used synthesis, represented by scheme 4, involves intermediates of Schiff base type[43]. The cyclization is generally carried out with nitroethane or diethyl malonate. Copper(II) complexes based on cyclam (2323) but also on macrocycles of different sizes (2223), (2333) or (3333) C-substituted by ester functional groups or nitro groups were thus obtained[43-46]. Free ligands mono- or di-C -functionalized by acid or amine groups can also be obtained starting from these complexes[47-50]. Bismacrocycles were also synthesized in this way[51]. The subsequent functionalization of the cyclam carrying an amino group, for example, makes possible access to new C-substituted macrocycles[52]. The yields observed during the cyclization reactions vary from 15 to 75% according to the compounds targeted. The disadvantages of the method are the removal of the metal ion, which requires conditions which limit the choice of the functional group introduced, and the impossibility of it being adapted to the cyclen series.

The use of Fe(III) as support has recently made it possible to obtain several C-arylated cyclens with yields of 40% to 70%[53-54].

Finally, some authors describe the synthesis of C-functionalized cyclens according to conditions of high dilution[28, 55-58]. These high-dilution techniques, which are widely used in the field of macrocyclic chemistry, generally result in good cyclization yields but the high dilution constitutes a major obstacle to the preparation of said macrocycles on a large scale.

The inventors have thus sought to develop a novel process for the preparation of C-functionalized tetraazacycloalkanes.

SUMMARY OF THE INVENTION

A subject matter of the invention is a process for the preparation of a compound of formula (I):

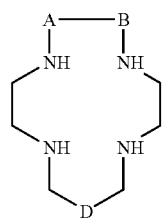
(I)

wherein:
one of the groups A or B represents a -$CH_2$- radical and the other group represents either a -$CH(R')$-$CH_2$- radical in which R' represents either a saturated or unsaturated aliphatic radical comprising from 1 to 12 carbon atoms or a -$(CH_2)_n$-O-$R_1'$ radical in which n represents an integer between 0 and 4 and $R_1'$ represents a hydrogen atom or a saturated or unsaturated aliphatic radical comprising from 1 to 8 carbon atoms or a -$(CH_2)_n$-C(=O)-O-$R_1'$ radical in which n and $R_1'$ are as defined above or a -$(CH_2)_n$-$R_2'$ radical in which $R_2'$ represents an unsubstituted phenyl radical or a phenyl radical substituted by one or more radicals selected from the amino, nitro, chloro, bromo, iodo, methoxy or hydroxyl radicals, or a -CH(R")- radical in which R" represents either a saturated or unsaturated aliphatic radical comprising from 1 to 12 carbon atoms or a -$(CH_2)_n$-O-$R_1''$ radical in which n represents an integer between 0 and 4 and $R_1''$ represents a hydrogen atom or a saturated or unsaturated aliphatic radical comprising from 1 to 8 carbon atoms or a -$(CH_2)_n$-C(=O)-O-$R_1''$ radical in which n and $R_1''$ are as defined above or a -$(CH_2)_n$-$R_2''$ radical in which $R_2''$ represents an unsubstituted phenyl radical or a phenyl radical substituted by one or more radicals selected from the amino, nitro, chloro, bromo, iodo, methoxy or hydroxyl radicals,
and the group D represents a -$(CH2)_m$- radical in which m is equal to 0 or to 1, comprising the following successive reaction stages:
a stage (a) during which the compound of formula (II):

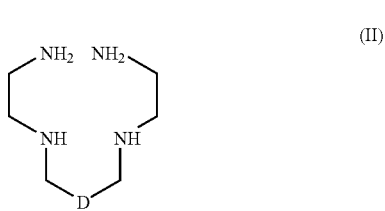
(II)

wherein the group D is as defined above, reacts with a compound of formula (III):

(III)

wherein R and $R_1$, which are identical or different, represent, independently of one another, a hydrogen atom or a radical selected from the methyl, ethyl, linear or branched propyl or linear or branched butyl radicals and preferably represent a hydrogen atom or a methyl radical, to form a compound of formula (IV):

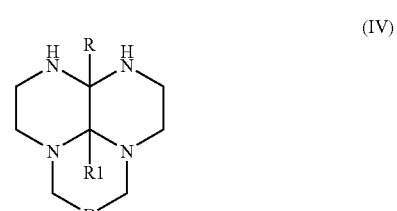
(IV)

wherein D, R and R1 are as defined above;
a stage (b) during which the compound of formula (IV) obtained in stage (a) reacts with the compound of formula (V):

(V)

wherein A and B are as defined above and X represents a radical selected from the bromo, iodo, chloro or tosylate radicals, to form the compound of formula (VI):

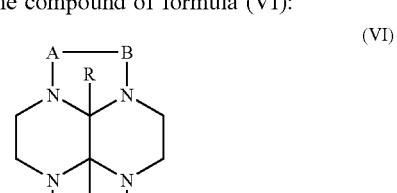
(VI)

wherein A, B, D, R and R1 are as defined above; and
a stage (c) during which the compound of formula (VI) obtained in stage (b) is subjected to an acid treatment, to form said compound of formula (I).

DETAILED DESCRIPTION OF THE INVENTION

Figure 1:
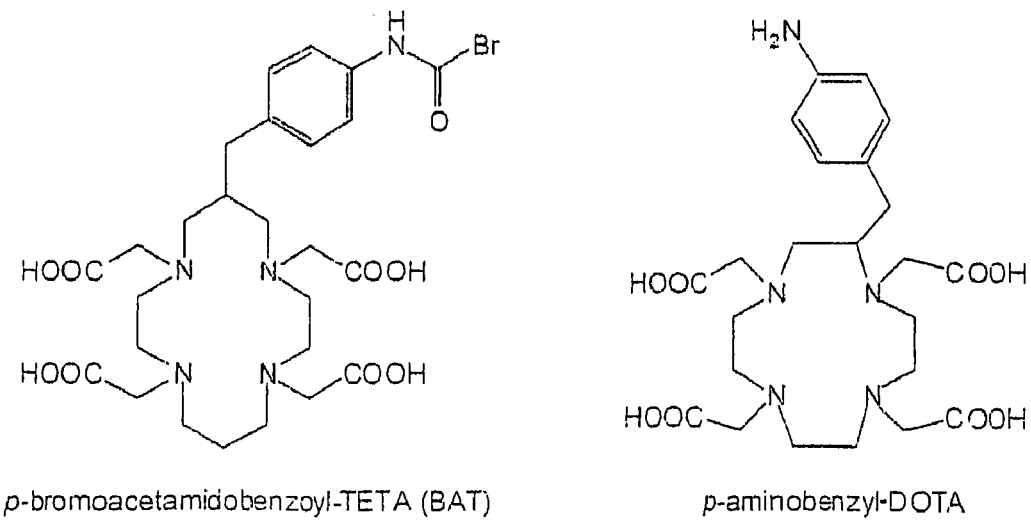
FIG. 1 shows bifunctional chelating agents.
Figure 2:
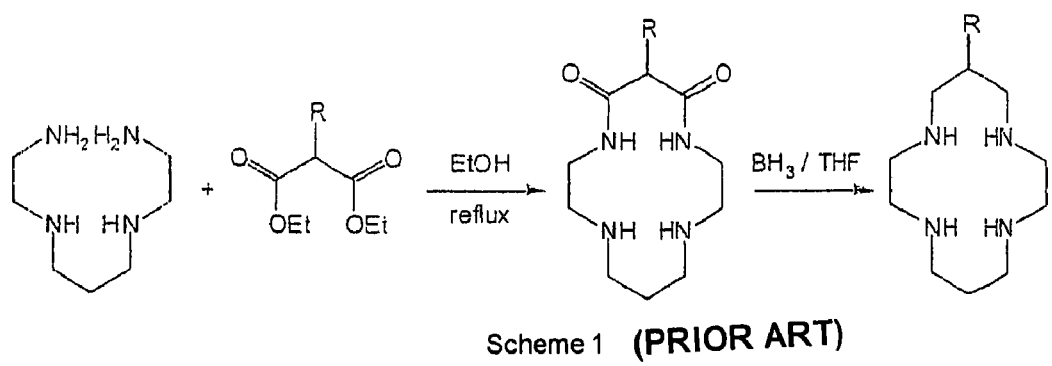
FIG. 2 shows reaction schemes 2 and 3, which relate to the N-functionalization of tetraazacycloalkanes.
Figure 2:
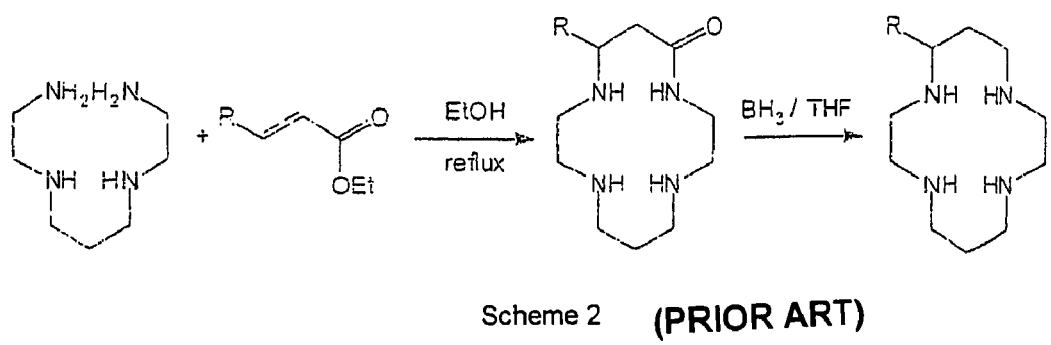
Figure 3:
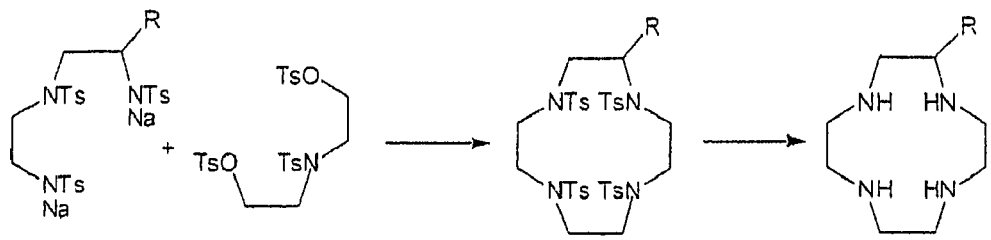
FIG. 3 shows reaction schemes 3 and 4, which relate to the N-functionalization of tetraazacycloalkanes.
Figure 3:
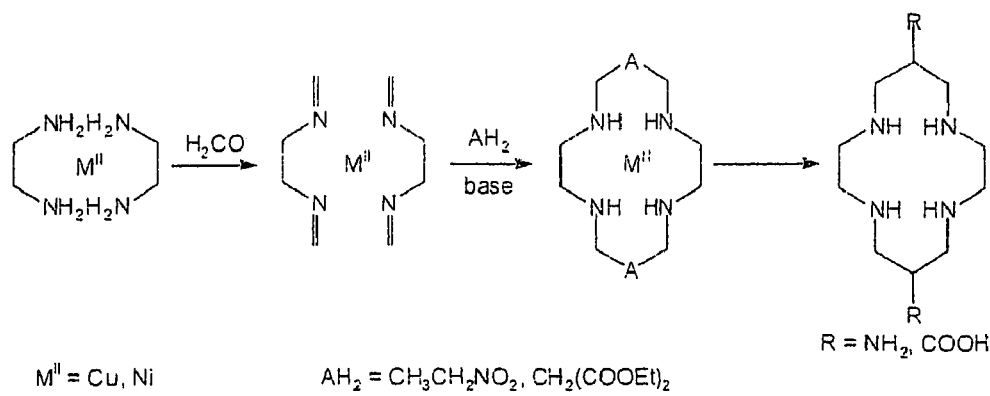
Figure 3:
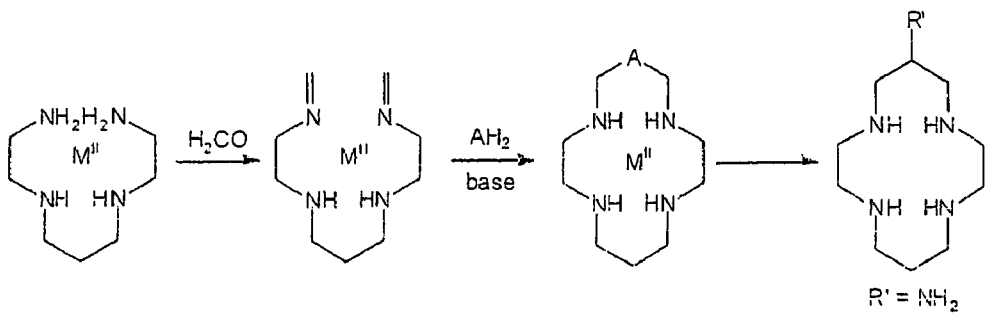
Figure 4:
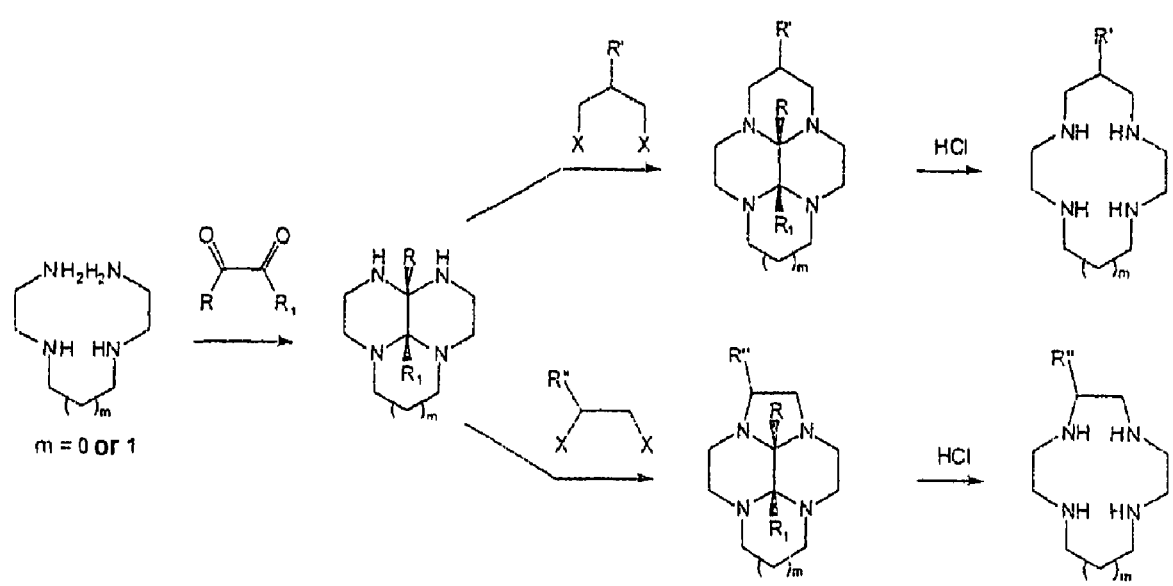
FIG. 4 shows reaction scheme 5.

The term "saturated or unsaturated aliphatic radical comprising from 1 to 12 carbon atoms" denotes, in the definitions of R', R", $R_1'$ and $R_1"$ described above, in particular alkyl radicals and alkenyl radicals.

Among the alkyl radicals, the following are denoted more particularly for R', R", $R_1'$ and $R_1"$: the methyl, ethyl, propyl, 1-methylethyl, butyl, 1-methylpropyl, 2-methylpropyl, 1,1-dimethylethyl, pentyl, 1-methyl-butyl, 2-methylbutyl, 1-ethylpropyl, 1,1-dimethyl-propyl, 2,2-dimethylpropyl or 1,2-dimethylpropyl radicals.

Among the alkenyl radicals, the following are denoted more particularly for R', R", $R_1'$ and $R_1"$: the vinyl, 1-propenyl, 1-methylethenyl, 2-propenyl, 1-butenyl, 1-methyl-1-propenyl, 2-methyl-1-propenyl, 2-butenyl, 1-pentenyl, 1-methyl-1-butenyl, 2-methyl-1-butenyl, 3-methyl-1-butenyl, 1,1-dimethyl-1-propenyl, 2,2-di-methyl-1-propenyl, 1,2-dimethyl-1-propenyl, 2-pentenyl or 2-methyl-2-butenyl radicals.

As illustrated by the examples described below, the process as defined above makes possible the direct synthesis of C-functionalized tetraazacycloalkanes, which are macrocycles of high added value. It is carried out in only three stages, starting from commercially available compounds. None of the three stages requires specific conditions: high dilution, inert atmosphere, long reaction times, and the like, in contrast to all the syntheses described to date. It is general and makes possible the preparation of C-functionalized cyclams and cyclens but also of 1,4,7,10-tetraazatridecanes (2223). The yields are very high (71-87% in the cyclam series) for such compounds. The mild conditions, in particular during the final "deprotection" stage, make possible the introduction of highly varied organic functional groups, in contrast to the methods involving reduction, detosylation or demetallation stages. A multitude of biselectrophilic ethane or propane derivatives can thus be used, even if the examples described here are limited to commercially available compounds. After N-functionalization by suitable groups, the diversity of the functional groups introduced at a carbon atom of the ring makes it possible to adapt the method of immobilization of the macrocycle on an antibody or on a solid support according to a given application. Finally, novel C-functionalized macrobicycles based on cyclam or on cyclen can be prepared according to this method. For this reason, another subject matter of the invention is the compounds of formula (VI) as defined above. The compounds of formula (VI) also make possible access to the compounds of formula (VII):

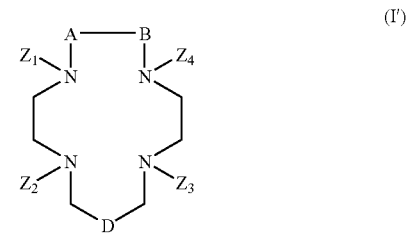

wherein A, B, D, R and R1 are as defined above, by an appropriate treatment within the scope of a person skilled in the art.

This compound of formula (VII) constitutes another subject matter of the present invention.

According to a specific aspect, another subject matter of the present invention is the compounds of formula (Ia):

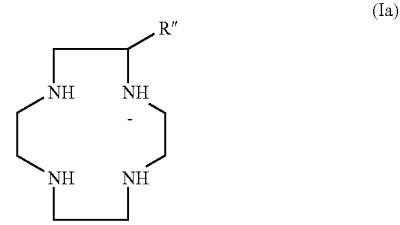

namely the two compounds of formula (I) as defined above for which A represents a -$CH_2$- group and B represents a -CH(R")- group and for which, in the definition of D, m is equal to 0, it being understood that, in the formula (Ia), R" does not represent a hydroxymethyl radical.

The compounds of formula (I) resulting from stage (c) of the process of the invention (and in particular the compounds of formula (Ia) as defined above where R" does or does not denote a hydroxymethyl radical) can be subjected to a subsequent stage (d) which consists in functionalizing one or more of the nitrogen atoms of their tetraazacycloalkane ring, whereby a compound is obtained which has the following formula (I'):

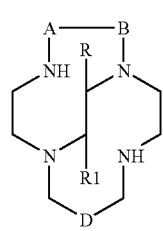

wherein:
  the groups A, B and D have the meanings mentioned above for the compounds of formula (I); and
  each of the groups $Z_1$, $Z_2$, $Z_3$ and $Z_4$ (which are identical or different) represents, independently of the other groups:
    a hydrogen atom,; or else
    a linear or branched alkyl radical comprising from 1 to 15 carbon atoms or a [hetero(aryl)] alkyl radical comprising from 7 to 12 carbon atoms; or else
    a -$(CH_2)_w$-Y radical, in which:
      w represents a number greater than zero and less than or equal to 6 and more particularly less than or equal to 3; and
      Y represents:
        a $[-C(=O)]_y$-V radical, in which:
          y is equal to 0 or to 1; and
          V represents an OH radical or an $OR_3$ radical (in which $R_3$ represents an alkyl radical comprising from 1 to 6 carbon atoms and more particularly from 1 to 3 carbon atoms, optionally substituted by one or more COOH, $SO_3H$, $PO_3H_2$ or $CO(NH_2)$ groups, or an $NH_2$, $NHR_4$ or N $(R_4)(R_5)$ radical (in which $R_4$ and $R_5$ represent an alkyl radical comprising from 1 to 4 carbon atoms); or else a -P(=O) (OR$_6$) (OR$_7$) radical in which $R_6$ and $R_7$ each independently represent a hydrogen atom or an alkyl radical comprising from 1 to 4 carbon atoms; or else an -SO$_3$H radical.

The functionalization of stage (d) can be obtained by an appropriate treatment within the scope of a person skilled in the art.

According to another aspect, another subject matter of the present invention is the process for the preparation of the compounds of formula (I') comprising the additional stage (d) defined above.

More particularly, another subject matter of the invention is the compounds capable of being obtained by subjecting the compounds of formula (Ia) to the abovementioned functionalization stage (d), namely the compounds of following formula (Ia'):

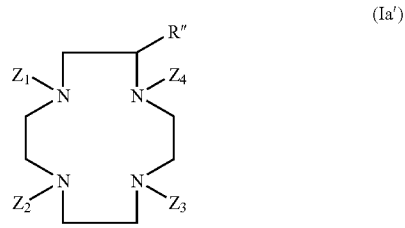

(Ia')

wherein R" and $Z_1$, $Z_2$, $Z_3$ and $Z_4$ have the abovementioned definitions.

The following examples illustrate the invention without, however, limiting it.

EXAMPLE A

Synthesis of methyl 1,4,8,11-tetraazacyclo-tetradecane-6-carboxylate (compound 5)

(a) Preparation of 9a,9b-dimethyloctahydro-1,3a,6a,9-tetra-azaphenalene (compound 1)

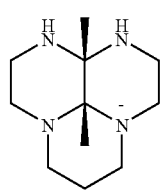

(1)

A solution of 5.37 g (62.4 mmol) of butanedione in 30 ml of acetonitrile is slowly added dropwise to a solution of 10.00 g (62.4 mmol) of commercial N,N'-bis (2-aminoethyl)-1,3-propanediamine in 100 ml of acetonitrile at 0° C. The mixture is maintained at this temperature for two hours. After evaporating the solvent, compound 1 is isolated quantitatively in the form of a yellow solid and is used for the following stage without subsequent purification.

$^{13}$C NMR spectrometry (125 MHz, CDCl$_3$, δ in ppm) 10.7, 18.3, 23.3, 39.2, 42.0, 45.6, 46.6, 49.0, 51.1, 68.1, 73.3.

Mass spectrometry: (MALDI-TOF) m/z =210 M$^{+•}$ (b) Preparation of methyl 10b,10c-dimethyldecahydro-3a,5a,8a,10a-tetraazapyrene-2-carboxylate (compound 3)

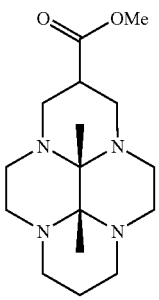

(3)

A solution of 4.95 g (19.0 mmol) of methyl 3-bromo-2-(bromomethyl) propanoate in 20 ml of acetonitrile is slowly added dropwise to a solution of 4.00 g (19.0 mmol) of compound 1 prepared in the preceding stage and of 13.15 g (95.0 mmol) of potassium carbonate (K$_2$CO$_3$) in 100 ml of acetonitrile at reflux. The solution is vigorously stirred and reflux is maintained for 48 hours. After filtering through celite and evaporating, compound 3 is obtained in the form of an orange-colored oil (5.58 g, Yield =95%).

$^{13}$C NMR spectrometry (125 MHz, CDCl$_3$, δ in ppm) 9.9, 10.6, 17.9, 35.4, 44.7, 46.3, 46.4, 46.6, 47.9, 48.9, 50.2, 50.4, 52.1, 73.2, 73.8, 174.6.

Mass spectrometry: (MALDI-TOF): m/z =308 M$^{+•}$ (c) Preparation of methyl 1,4,8,11-tetraazacyclotetra-decane-6-carboxylate (compound 5)

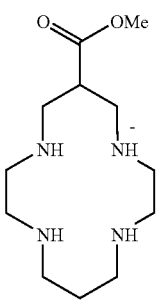

(5)

A solution of 5.00 g (16.2 mmol) of compound 3 prepared in the preceding stage in 50 ml of absolute methanol is brought to reflux. 30 ml of a 35% aqueous hydrochloric acid solution are added in small amounts. Reflux is maintained for 48 hours. The mixture is cooled to 0° C. and the precipitate formed is filtered off and then washed with ice-cold methanol. The filtrate is evaporated and then the residue is taken up in the minimum amount of methanol. The precipitate formed is filtered off and washed with ice-cold methanol. Compound 5·4HCl is isolated in the form of a white powder (4.55 g, Yield =76%). Overall yield starting from the tetraamine: 72%.

$^1$H NMR spectrometry (500 MHz, D$_2$O, δ in ppm): 2.22 (qt, 2H), 3.10-3.80 (m, 17H), 3.78 (s, 3H). $^{13}$C NMR spectrometry (125 MHz, D$_2$O, δ in ppm): 21.9, 38.3, 41.7, 42.4, 44.5, 46.9, 56.5, 173.5.

Mass spectrometry: (MALDI-TOF): m/z =259 (M+H)$^{+•}$

EXAMPLE B

Synthesis of 1,4,8,11-tetraazacyclotetra-decane-6-carboxylic acid (compound 6)

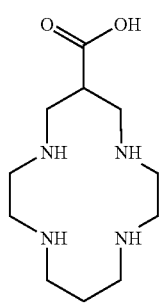
(6)

A solution of 0.50 g (1.62 mmol) of compound 3, prepared in example A, stage (b), in 20 ml of absolute ethanol is brought to reflux. 3 ml of a 35% aqueous hydrochloric acid solution are added in small amounts. Reflux is maintained for 48 hours. The mixture is cooled to 0° C. and the precipitate formed is filtered off and washed with ice-cold ethanol. The filtrate is evaporated and then the residue is taken up in the minimum amount of ethanol. The precipitate formed is filtered off and washed with ice-cold ethanol. Compound 6·3HCl is isolated in the form of a white powder (0.57 g, Yield =92%). Overall yield starting from the tetraamine: 87%.

$^1$H NMR spectrometry (500 MHz, D$_2$O, δ in ppm): 1.55 (qt, 2H), 2.64 (qt, 1H), 2.70-3.00 (m, 16H). $^{13}$C NMR spectrometry (125 MHz, D$_2$O, δ in ppm): 22.3, 38.6, 42.3, 42.7, 44.8, 46.9, 175.7.

Elemental analysis for C$_{11}$H$_{24}$N$_4$O$_2$·3HCl·3H$_2$O: Calculated: C 32.40%; H, 8.16%; N, 13.74% Found: C 32.66%; H, 8.03%; N, 13.81%

EXAMPLE C

Synthesis of 1,4,8,11-tetraazacyclodecan-6-ol (compound 7)

(a) Preparation of 10b,10c-dimethyldecahydro-3a,5a,8a,10a-tetraazapyren-2-ol (compound 4)

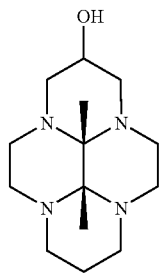
(4)

This product is obtained according to a procedure identical to that described in example A, stage (b), from 8.00 g (38.1 mmol) of compound 1, 8.36 g (38.1 mmol) of 1,3-dibromopropan-2-ol and 26.32 g (190.5 mmol) of K$_2$CO$_3$. Compound 4 is isolated in the form of an orange oil (9.00 g, Yield =90%), composed of two isomers.

Mass spectrometry: (MALDI-TOF): m/z =267 (M+H)$^{+\bullet}$ (b) Preparation of 1,4,8,11-tetraazacyclodecan-6-ol (compound 7)

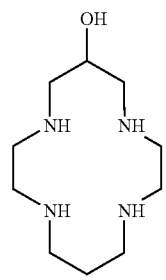
(7)

This product is obtained according to a procedure identical to that described in example B from 1.15 g (4.31 mmol) of compound 4 prepared in the preceding stage. Compound 7·4HCl is isolated in the form of an off-white powder (1.23 g, Yield =79%). Overall yield starting from the tetraamine: 71%.

$^1$H NMR spectrometry (200 MHz, D$_2$O, δ in ppm): 2.11 (qt, 2H), 2.8-3.8 (m, 17H). $^{13}$C NMR spectrometry (50 MHz, D$_2$O, δ in ppm): 23.8, 43.8, 45.3 (x2), 46.1 (x2), 46.7, 50.3, 59.5, 61.7.

Mass spectrometry: (MALDI-TOF): m/z =217 (M+H)$^{+\bullet}$

EXAMPLE D

Synthesis of 1,4,7,10-tetraazacyclotridec-5-ylmethanol (compound 9)

(a) Preparation of 9b,9c-dimethyldecahydro-2a,4a,7a,9a-tetraazacyclopenta[cd]phenalen-1-ylmethanol (compound 8)

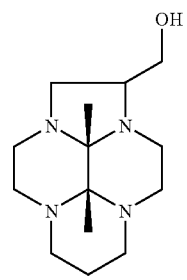
(8)

This product is obtained according to a procedure identical to that described in example A, stage (b), from 1.00 g (4.73 mmol) of compound 1, 1.05 g (4.73 mmol) of 2,3-dibromopropan-1-ol and 3.27 g (23.65 mmol) of K$_2$CO$_3$. Compound 8 is isolated in the form of an orange-colored oil (1.20 g, Yield =95%) composed of several isomers.

Mass spectrometry: (MALDI-TOF): m/z =267 (M+H)$^{+\bullet}$ (b) Preparation of 1,4,7,10-tetraazacyclotridec-5-yl-methanol (compound 9)

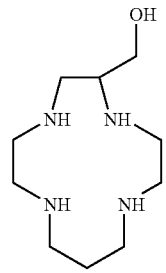
(9)

This product is obtained according to a procedure identical to that described in example d from 1.20 g (4.51 mmol) of compound 8 prepared in the preceding stage. Compound 9 is isolated in the form of an off-white powder (0.93 g, Yield =54%). Overall yield starting from the tetraamine: 52%. $^{13}$C NMR spectrometry (125 MHz, D$_2$O, δ in ppm): 29.0, 46.4, 47.9, 49.1, 49.3, 50.1, 50.1, 50.4, 58.5, 63.4.

Mass spectrometry: (MALDI-TOF): m/z =217 (M+H)$^{+•}$

EXAMPLE E

Synthesis of 1,4,7,10-tetraazacyclododec-2-ylmethanol (compound 11)

(a) Preparation of 5a,8b-dimethyloctahydro-2a,5,6,8a-tetraazaacenaphthylene (compound 2)

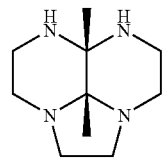
(2)

This product is obtained according to a procedure identical to that described in example A, stage (a), from 10.00 g (68.4 mmol) of triethylenetetraamine and 5.88 g (68.4 mmol) of butanedione. Compound 2 is isolated quantitatively in the form of an amber solid and is used for the following stage without subsequent purification.

Mass spectrometry: (MALDI-TOF): m/z =197 (M+H)$^{+•}$ (b) Preparation of 8b,8c-dimethyldecahydro-2a,4a,6a,8a-tetraazacyclopenta[fg]acenaphthylen-1-ylmethanol (compound 10)

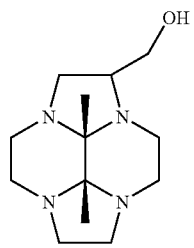
(10)

A solution of 5.58 g (25.5 mmol) of 2,3-dibromopropan-1-ol in 20 ml of acetonitrile is slowly added dropwise to a solution of 5.00 g (25.5 mmol) of compound 2 prepared in the preceding stage and of 17.54 g (127 mmol) of K$_2$CO$_3$ in 125 ml of acetonitrile at reflux. The solution is vigorously stirred and reflux is maintained for 48 hours. After filtration through celite, evaporation and chromatography of the oil obtained on an alumina column (eluent CH$_3$OH/CH$_2$Cl$_2$3/100), compound 10 is obtained in the form of an orange oil (3.10 g, Yd =48%) composed of several isomers.

Mass spectrometry: (MALDI-TOF): m/z =253 (M+H)$^{+•}$ (c) Preparation of 1,4,7,10-tetraazacyclododec-2-yl-methanol (compound 11)

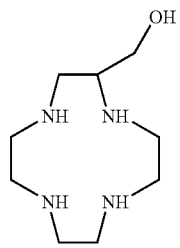
(11)

A solution of 1.00 g (3.99 mmol) of compound 10 obtained in the preceding stage in 50 ml of absolute ethanol is brought to reflux. 10 ml of a 35% aqueous hydrochloric acid solution are added in small amounts. Reflux is maintained for 48 hours. After evaporation of the solvents, the residue is taken up in the minimum amount of ice-cold ethanol. The precipitate formed is filtered off and washed with ice-cold methanol. The filtrate is evaporated and then the residue is taken up in the minimum amount of methanol. The precipitate formed is filtered off and washed with ice-cold methanol. Compound 11·4HCl is isolated in the form of a white powder (0.80 g, Yd =57%).

Overall yield starting from the tetraamine: 27%.

$^{13}$C NMR spectrometry (125 MHz, D$_2$O, δ in ppm): 42.1, 43.3, 43.9, 44.0, 44.5, 44.9, 46.9, 56.0, 59.5.

Mass spectrometry: (MALDI-TOF): m/z =203 (M+H)$^{+•}$

EXAMPLE F

Synthesis of methyl decahydro-3a,5a,8a,10a-tetraazapyrene-2-carboxylate (compound 13)

(a) Preparation of octahydro-1,3a,6a,9-tetraaza-phenalene (compound 12)

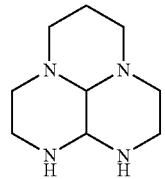
(12)

9.04 g (62.4 mmol) of a 40% by weight aqueous glyoxal solution are slowly added dropwise to a solution of 10.00 g (62.4 mmol) of N,N'-bis(2-aminoethyl)-1,3-pro-panediamine in 30 ml of water at 0° C. The mixture is maintained at this temperature for 1 hour and then stirred at ambient temperature for 10 hours. After evaporation of the water, compound 12 is isolated quantitatively in the form of a pale yellow solid and is used for the following stage without subsequent purification.

$^{13}$C NMR spectrometry (50 MHz, CDCl$_3$, δ in ppm) 19.8, 54.0-55.5 (broad), 67.3, 77.3.

(b) Preparation of methyl decahydro-3a,5a,8a,10a-tetra-azapyrene-2-carboxylate (compound 13)

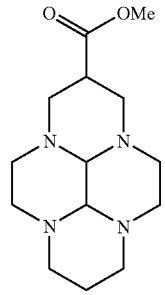
(13)

This product is obtained according to a procedure identical to that described in example A, stage (b), from 1 g (5.48 mmol) of compound 12 prepared in the preceding stage, 1.42 9 (5.48 mmol) of methyl 3-bromo-2-(bromomethyl) propanoate and 3.80 g (27.45 mmol) of K$_2$CO$_3$. Compound 13 is isolated in the form of an orange oil (1.46 9, Yd =95%) composed of two isomers.

EXAMPLE G

Synthesis of decahydro-2a,4a,6a,8a-tetraaza-cyclopenta [fg] acenaphthylen-1-ylmethanol (compound 15)

(a) Preparation of octahydro-2a,5,6,8a-tetraazaace-naphthylene (compound 14)

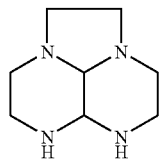

(14)

This product is obtained according to a procedure identical to that described in example F, stage (a), from 5.00 g (34.2 mmol) of triethylenetetraamine and 4.95 g (34.2 mmol) of a glyoxal solution (40% in $H_2O$). Compound 14 (4 isomers) is isolated quantitatively in the form of a yellow oil and is used for the following stage without subsequent purification.

Mass spectrometry: (MALDI-TOF): m/z =169 (M+H)$^{+\cdot}$ (b) Preparation of decahydro-2a,4a,6a,8a-tetraaza-cyclopenta [fg] acenaphthylen-1-ylmethanol (compound 15)

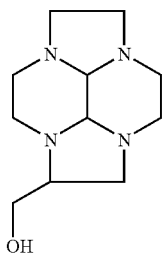

(15)

This product is obtained according to a procedure identical to that described in example A, stage (b), from 3.00 g (17.87 mmol) of compound 14 prepared in the preceding stage, 3.92 g (17.87 mmol) of 2,3-dibromo-propan-1-ol and 12.34 g (89.3 mmol) of $K_2CO_3$. Compound 15 is isolated in the form of a red oil (3.95 g).

EXAMPLE H

Synthesis of 1-(1,4,7,10-tetraazacyclotri-dec-5-yl) allyloxymethane (compound 18)

(a) Preparation of 3-allyloxy-1,2-propanediol ditosyl-ate (compound 16)

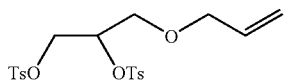

A solution of 216.7 g of p-TsCl (1.13 mmol) in 300 ml of pyridine is cooled to -5° C. A solution of 50 g of 3-allyloxy-1,2-propanediol (0.38 mol) is slowly added. At the end of the addition, the mixture is maintained at ambient temperature and is stirred for 12 h. The precipitate formed is then filtered off and the filtrate is evaporated. The oil obtained is taken up in 50 ml of chloroform and is washed with 200 ml of a 0.5M HCl solution and then with 200 ml of a 1M $Na_2CO_3$ solution. After evaporation of the organic phase, compound 16 is isolated in the form of a yellow oil (142.39 g, Yd =85%).

$^1$H NMR (200 MHz, CDCl$_3$): 2.33 (s, 6H), 3.44 (d, 2H), 3.72 (m, 2H), 4.07 (m, 2H), 4.61 (m, 1H), 4.99–5.10 (m, 2H), 5.52–5.71 (m, 1H) 7.20 (m, 4H), 7.55–7.70 (m, 4H).

$^{13}$C NMR (50 MHz, CDCl$_3$): 21.7 (x2), 67.5, 67.7, 72.3, 77.0, 117.5, 127.9 (x3), 129.9 (x2), 133.8 (x2), 145.3 (x2).

(b) Preparation of 1-(9b,9c-dimethyldecahydro-2a,4a,7a,9a-tetraazacyclopenta[cd]phenalen-1-yl)allyl-oxymethane (compound 17)

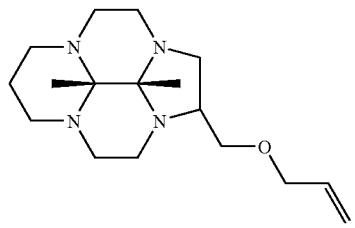

This product is obtained according to a procedure identical to that described in example A, stage (b), from 26.2 g (0.12 mol) of compound 1, 54.9 g (0.12 mol) of compound 16 and 86 g (0.62 mol) of $K_2CO_3$. The red oil obtained is purified by chromatography on an alumina column (eluent $CH_2Cl_2$). Compound 17 is obtained in the form of a yellow oil (8.6 g, Yd =22%) composed of two isomers.

Mass spectrometry: (MALDI-TOF): m/z =306 (M$^{+\cdot}$)

(c) Preparation of 1-(1,4,7,10-tetraazacyclotridec-5-yl)ally-loxymethane (compound 18)

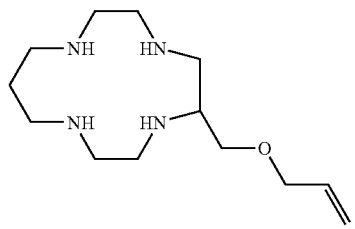

This product is obtained according to a procedure identical to that described in example B from 0.8 g (2.61 mmol) of compound 17. Compound 18·4HCl is isolated in the form of an off-white powder. This powder is dissolved in the minimum amount of water and the solution is brought to basic pH by addition of NaOH pellets. After extraction with 3×100 ml of chloroform and drying over MgSO$_4$, the solvents are evaporated.

Compound 18 is obtained in the form of a yellow oil (0.5 g, Yd =75%).

$^1$H NMR (500 MHz, CDCl$_3$): 1.34 (m, 2H), 1.96 (s, 4H), 2.16 (m, 1H), 2.25–2.55 (m, 14H), 3.01 (m, 1H), 3.10 (m, 1H), 3.63 (m, 2H), 4.81 (dd, 1H, J =1.0 Hz, 10.5 Hz), 4.91 (dd, 1H, J =1.5 Hz, 15.5 Hz), 5.55 (m, 1H, J =5.5 Hz, 10.5 Hz, 15.5 Hz).

$^{13}$C NMR (125 MHz, CDCl$_3$): (CH$_2$-β) 29.1, (CH$_2$-α) 46.2, 47.8, 48.9, 49.2, 49.9, 49.8, 50.4, (CH-) 56.8, (CH$_2$-O) 72.1, 72.4, (CH$_2$=C) 116.8, (CH=) 134.8.

Mass spectrometry: (MALDI-TOF): m/z =256.89 (M$^{+\cdot}$)

Elemental analysis for $C_{13}H_{28}N_4O \cdot H_2O$: Calculated: C 56.89; H 11.03; N 20.42 Found: C 57.39; H 10.98; N 19.94

EXAMPLE I

Preparation of methyl 1,4,8,11-tetraethoxy-carbonylmethyl-1,4,8,11-tetraazacyclotetradecane-6-carboxylate (compound 19)

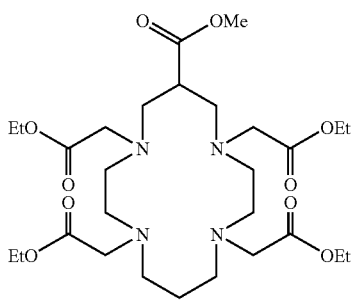

A solution of 1 g (2.5 mmol) of compound 5·4HCl, prepared in example A, stage (c), and 6.8 g (0.50 mol) of $K_2CO_3$ in 500 ml of acetonitrile is brought to reflux. 1.65 g (9.9 mmol) of ethyl 2-bromoacetate are then added. Reflux is maintained for 6 days. After filtration and evaporation of the solvent, the red oil obtained is purified by chromatography on an alumina column (eluent $CH_2Cl_2$). Compound 19 is obtained in the form of a yellow oil (0.9 g, Yd =60%).

$^{13}C$ NMR (125 MHz, $CDCl_3$): 14.8 (x4), 25.7, 45.2, 51.5 (x2), 52.1 (x2), 52.2, 55.6 (x2), 55.7 (x2), 56.0 (x2), 56.7 (x2), 60.7 (x4), 172.2 (x4), 176.1.

EXAMPLE J

Preparation of (1,4,7,10-tetra(N,N-di-methylcarbamoylmethyl)-1,4,7,10-tetraazacyclotridec-5-yl)methanol (compound 20)

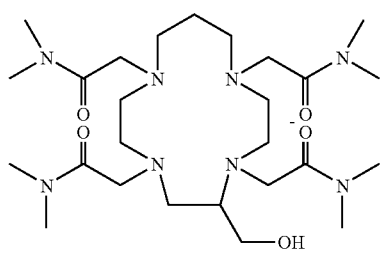

This product is obtained according to a procedure identical to that described in example I from 7.7 g (35.6 mmol) of compound 9 and 21.66 g (176.2 mmol) of 2-chloro-N,N-dimethylacetamide. The red oil obtained is purified by chromatography on an alumina column (eluent $CH_2Cl_2$/MeOH 98/2). Compound 20 is obtained in the form of a yellow oil (5.5 g, Yd =28%).

$^1H$ NMR (500 MHz, $CDCl_3$) 1.56 (m, 2H, J=6.3 Hz), 2.39 (m, 1H), 2.45-3.10 (m, 14H), 2.85 (s, 3H), 2.87 (s, 9H), 2.93 (s, 3H), 2.97 (s, 3H), 3.01 (s, 3H), 3.02 (s, 3H), 3.15-3.6 (m, 11H).

$^{13}C$ NMR (125 MHz, $CDCl_3$): ($CH_2$-β) 24.2, ($CH_3$-N) 35.8 (x3), 36.1, 36.8, 37.1, 37.4 (x2), ($CH_2$-α, CH-α) 50.8 (x2), 50.9, 51.5, 52.1 (x2), 54.7, 54.8, ($CH_2$-CO) 57.4 (x2), 58.0, 60.2, ($CH_2$-OH) 62.5, (C=O) 170.9, 171.0, 171.1, 172.8.

Mass spectrometry: (MALDI-TOF): m/z =557.71 ($M^{+\cdot}$)

EXAMPLE K

Preparation of (1,4,7,10-tetra(N,N-dimethyl-carbamoylmethyl)-1-(1,4,7,10-tetraazacyclotridec-5-yl)allyloxymethane (compound 21)

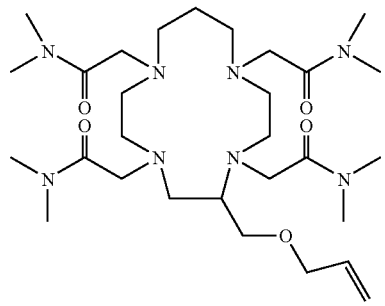

This product is obtained according to a procedure identical to that described in example 1 from 4.9 g (19.1 mmol) of compound 18 and 9.3 g (76.6 mmol) of 2-chloro-N,N-dimethylacetamide. The red oil obtained is purified by chromatography on an alumina column (eluent $CH_2Cl_2$/MeOH 99/1). Compound 21 is obtained in the form of a yellow oil (4.15 g, Yd =36%).

$^1H$ NMR (500 MHz, $CDCl_3$): 1.40 (m, 2H), 2.3-3.5 (m, 49H), 3.72 (m, 2H), 4.93 (d, 1H, J=10.3 Hz), 5.05 (dd, 1H, J=1.8 Hz, 17 Hz), 5.60 (m, 1H).

$^{13}C$ NMR (125 MHz, $CDCl_3$) ($CH_2$-β) 23.4, ($CH_3$-N) 35.6 (x2), 35.7, 35.9, 37.1, 37.2, 37.3, 37.5, ($CH_2$-α, CH-α) 49.8, 50.9, 51.9, 52.2 (x2), 53.2, (x2), 55.4, ($CH_2$-CO) 57.3, 57.6, 57.5, 58.2, ($CH_2$-O) 69.7, 72.2, ($CH_2$=) 116.5, (CH=) 135.2, (C=O) 170.5, 170.8, (x2), 171.1.

Mass spectrometry: (MALDI-TOF): m/z =597.41 ($M^{+\cdot}$)

BIBLIOGRAPHIC REFERENCES (1) Tabushi, I.; Taniguchi, Y.; Kato, H.; *Tetrahedron Lett.*, 1977, 12, 1049-1052.

(2) Tabushi, I.; Fujiyoshi, M.; *Heterocycles*, 1977, 7, 851-855.

(3) Kimura, E.; Koike, T.; Machida, R.; Nagai, R.; Kodama, M.; *Inorg. Chem.*, 1984, 23, 4181-4188.

(4) Moi, M. K.; Meares, C. F.; McCall, M. J.; Cole, W. C.; DeNardot, S. J.; *Anal. Biochem.*, 1985, 148, 249-253.

(5) Meares, C. F.; DeNardo, S. J.; Cole, W. C., Mol, M. K., U.S. Pat. No. 4 678 667, 1987.

(6) Morphy, J. R.; Parker, D.; Alexander, R.; Bains, A.; Carne, A. F.; Eaton, M. A. W.; Harrison, A.; Millican, A.; Phipps, A.; Rhind, S. K.; Titmas, R.; Weatherby, D.; *J. Chem. Soc. Chem. Commun.*, 1988, 156-158.

(7) Takenouchi, K.; Watanabe, K.; Kato, Y.; Koike, T.; Kimura, E.; *J. Org. Chem.*, 1993, 58, 1955-1958.

(8) Kruper, W. J.; Pollock, D. K.; Fordyce, W. A.; Fazio, M. J.; Inbasekaran, M. N.; Muthyala, R., U.S. Pat. No. 5 489 425, 1996.

(9) Zhu, S.; Kou, F.; Lin, H.; Lin, C.; Lin, M.; Chen, Y.; *Inorg. Chem.*, 1996, 35, 5851-5859.

(10) Matheson, R. C., WO 00/21941, 2000.

(11) McAuley, A.; Subramanian, S.; *Inorg. Chim. Acta*, 2000, 300, 477-486.
(12) Buttafava, A.; Fabbrizzi, L.; Perotti, A.; Seghi, B.; *J. Chem. Soc. Chem. Commun.*, 1982, 1166-1167.
(13) Inouye, Y.; Kanamori, T.; Sugiyama, M.; Yoshida, T.; Koike, T.; Shionoya, M.; Enomoto, K.; Suehiro, K.; Kimura, E.; *Antivir. Chem. Chemother.*, 1995, 6, 337-344.
(14) Kido, H.; Takada, M.; Suwabe, M.; Yamaguchi, T.; Ito, T.; *Inorg. Chim. Acta*, 1995, 228, 133-138.
(15) Ruser, G.; Ritter, W.; Maecke, H. R.; *Bioconjugate Chem.*, 1990, 1, 345-349.
(16) Zhu, S. R.; Lin, H. K.; Lin, C. C.; Kou, F. P.; Chen, Y. T.; *Inorg. Chim. Acta*, 1995, 228, 225-232.
(17) Wöhrle, D.; Nicolaus, V.; *Polym. Bull.*, 1986, 15, 185-192.
(18) Nicolaus, V.; Woehrle, D.; *Angew. Makromol. Chem.*, 1992, 198, 179-190.
(19) Moran, J. K.; Greiner, D. P.; Meares, C. F.; *Bioconjugate Chem.*, 1995, 6, 296-301.
(20) Moreau, P.; Tinkl, M.; Tsukazaki, M.; Bury, P. S.; Griffen, E. J.; Snieckus, V.; Maharajh, R. B.; Kwok, C. S.; Somayaji, V. V.; Peng, Z.; Sykes, T. R.; Noujaim, A. A.; *Synthesis*, 1997, 1010-1012.
(21) Kimura, E.; Koike, T.; Takahashi, M.; *J. Chem. Soc. Chem. Commun.*, 1985, 385-386.
(22) Kimura, E.; Koike, T.; Uenishi, K.; Hediger, M.; Kuramoto, M.; Joko, S.; Arai, Y.; Kodama, M.; Iitaka, Y.; *Inorg. Chem.*, 1987, 26, 2975-2983.
(23) Kimura, E.; Koike, T.; Nada, H.; Iitaka, Y.; *J. Chem. Soc. Chem. Commun.*, 1986, 1322-1323.
(24) Kimura, E.; Shionoya, M.; Mita, T.; Iitaka, Y.; *J. Chem. Soc. Chem. Commun.*, 1987, 1712-1714.
(25) Kimura, E.; Kotake, Y.; Koike, T.; Shionoya, M.; Shiro, M.; *Inorg. Chem.*, 1990, 29, 4991-4996.
(26) Kimura, E.; Kodama, Y.; Shionoya, M.; Koike, T.; *Inorg. Chim. Acta*, 1996, 246, 151-158.
(27) Moi, M. K.; Meares, C. F.; DeNardo, S. J.; *J. Am. Chem. Soc.*, 1988, 110, 6266-6267.
(28) Gansow, O. A.; Kumar, K., U.S. Pat. No. 4 923 985, 1990.
(29) Garrity, M. L.; Brown, G. M.; Elbert, J. E.; Sachleben, R. A.; *Tetrahedron Lett.*, 1993, 34, 5531-5534.
(30) Ansari, M. H.; Ahmad, M.; Dicke, K. A.; *Bioorg. Med. Chem. Lett.*, 1993, 3, 1067-1070. p0 (31) Richman, J. E.; Atkins, T. J.; *J. Am. Chem. Soc.*, 1974, 96, 2268-2270.
(32) Deutsch, J.; Gries, H.; Conrad, J.; Weinmann, H. J., WO 88/08422, 1988.
(33) Parker, D.; Millican, T. A., WO 89/01476, 1989.
(34) Cox, J. P. L.; Jankowski, K. J.; Kataky, R.; Parker, D.; Beeley, N. R. A.; Boyce, B. A.; Eaton, M. A. W.; Millar, K.; Millican, A. T.; Harrison, A.; Walker, C.; *J. Chem. Soc. Chem. Cornnun.*, 1989, 797-798.
(35) Cox, J. P. L.; Craig, A. S.; Helps, I. M.; Jankowsky, K. J.; Parker, D.; Eaton, M. A. W.; Millican, A. T.; Millar, K.; Beeley, N. R. A.; Boyce, B. A.; *J. Chem. Soc. Perkin Trans. I*, 1990, 2567-2576.
(36) Schaefer, M.; Meyer, D.; Beaute, S.; Doucet, D.; *Magn. Reson. Med.*, 1991, 22, 238-241.
(37) Muller, F. R.; Handel, H.; *Tetrahedron Lett.*, 1982, 23, 2769-2772.
(38) Benabdallah, T.; Guglielmetti, R.; *Helv. Chim. Acta*, 1988, 71, 602-608.
(39) Wagler, T. R.; Burrows, C. J.; *J. Chem. Soc. Chem. Commun.*, 1987, 277-278.
(40) Marecek, J. F.; Burrows, C. J.; *Tetrahedron Lett.*, 1986, 27, 5943-5946.
(41) Barefield, E. K.; *Inorg. Chem.*, 1972, 11, 2273-2274.
(42) Guilard, R.; Meunier, I.; Jean, C.; Boisselier-Cocolios, B., EP 427 595, 1991.
(43) Comba, P.; Curtis, N. F.; Lawrance, G. A.; Sargeson, A. M.; Skelton, B. W.; White, A. H.; *Inorg. Chem.*, 1986, 25, 4260-4267.
(44) Lawrance, G. A.; O'Leary, M. A.; *Polyhedron*, 1987, 6, 1291-1294.
(45) Comba, P.; Curtis, N. F.; Lawrance, G. A.; O'Leary, M. A.; Skelton, B. W.; White, A. H.; *J. Chem. Soc. Dalton Trans.*, 1988, 497-502.
(46) Comba, P.; Curtis, N. F.; Lawrance, G. A.; O'Leary, M. A.; Skelton, B. W.; White, A. H.; *J. Chem. Soc. Dalton Trans.*, 1988, 2145-2152.
(47) Bernhardt, P. V.; Lawrance, G. A.; Hambley, T. W.; *J. Chem. Soc. Dalton Trans.*, 1989, 1059-1065.
(48) Lawrance, G. A.; Manning, T. M.; Maeder, M.; Martinez, M.; Oleary, M. A.; Patalinghug, W. C.; Skelton, B. W.; White, A. H.; *J. Chem. Soc. Dalton Trans.*, 1992, 1635-1641.
(49) Hambley, T. W.; Lawrance, G. A.; Maeder, M.; Wilkes, E. N.; *J. Chem. Soc. Dalton Trans.*, 1992, 1283-1289.
(50) Curtis, N. F.; Xin, L.; Weatherburn, D. C.; *Inorg. Chem.*, 1993, 32, 5838-5843.
(51) Comba, P.; Hilfenhaus, P.; *J. Chem. Soc. Dalton Trans.*, 1995, 3269-3274.
(52) Bernhardt, P. V.; Sharpe, P. C.; *Inorg. Chem.*, 2000, 39, 4123-4129.
(53) Edlin, C. D.; Faulkner, S.; Parker, D.; Wilkinson, M. P.; *Chem. Commun.*, 1996, 1249-1250. (54) Edlin, C. D.; Faulkner, S.; Parker, D.; Wilkinson, M. P.; Woods, M.; Lin, J.; Lasri, E.; Neth, F.; Port, M.; *New J. Chem.*, 1998, 1359-1364.
(55) Tundo, P.; *Tetrahedron Lett.*, 1978, 47, 4693-4696.
(56) McMurry, T. J.; Brechbiel, M.; Kumar, K.; Gansow, O. A.; *Bioconjugate Chem.*, 1992, 3, 108-117.
(57) Takenouchi, K.; Tabe, M.; Watanabe, K.; Hazato, A.; Kato, Y.; Shionoya, M.; Koike, T.; Kimura, E. *J.; Org. Chem.*, 1993, 58, 6895-6899.
(58) Mishra, A. K.; Gestin, J. F.; Benoist, E.; Faivrechauvet, A.; Chatal, J. F.; *New J. Chem.*, 1996, 20, 585-588.
(59) Sandnes, R. W.; Vasilevskis, J.; Undheim, K.; Gacek, M., WO 96/28432, 1996.
(60) Argese, M.; Ripa, G.; Scala, A.; Valle, V., WO 97/49691, 1997.
(61) Ripa, G.; Argese, M., WO 98/49151, 1998.
(62) Sandnes, R. W.; Gacek, M.; Undheim, K.; *Acta Chem. Scand.*, 1998, 52, 1402-1404.
(63) Hervé, G.; Bernard, H.; Le Bris, N.; Yaouanc, J. J.; Handel, H.; *Tetrahedron Lett.*, 1998, 39, 6861-6864.
(64) Hervé, G.; Bernard, H.; Le Bris, N.; Le Baccon, M.; Yaouanc, J. J.; Handel, H.; *Tetrahedron Lett.*, 1999, 40, 2517-2520.
(65) Platzek, J.; Hoyer, K.; Graske, K.-D.; Raduchel, B., WO 00/32581, 2000.
(66) Argese, M.; Manfredi, G.; Rebasti, F.; Ripa, G., WO 00/53588, 2000.
(67) Ferrari, M.; Giovenzana, G. B.; Palmisano, G.; Sisti, M.; *Synth. Commun.*, 2000, 30, 15-21.
(68) Hervé, G.; Bernard, H.; Toupet, L.; Handel, H.; *Eur. J. Org. Chem.*, 2000, 33-35.
(69) Weisman, G. R.; Wong, E. H.; Hill, D. C.; Rogers, M. E.; Reed, D. P.; Calabrese, J. C.; *Chem. Commun.*, 1996, 947-948.
(70) Hubin, T. J.; McCormick, J. M.; Collinson, S. R.; Alcock, N. W.; Busch, D. H.; *Chem. Commun.*, 1998, 1675-1676.

(71) Hubin, T. J.; McCormick, J. M.; Collinson, S. R.; Buchalova, M.; Perkins, C. M.; Alcock, N. W.; Kahol, P. K.; Raghunathan, A.; Busch, D. H.; *J. Am. Chem. Soc.*, 2000, 122, 2512-2522.
(72) Wong, E. H.; Weisman, G. R.; Hill, D. C.; Reed, D. P.; Rogers, M. E.; Condon, J. S.; Fagan, M. A.; Calabrese, J. C.; Lam, K. C.; Guzei, I. A.; Rheingold, A. L.; *J. Am. Chem. Soc.*, 2000, 122, 10561-10572.
(73) Hiler, G. D.; Perkins, C. M., WO 00/32601, 2000.

The invention claimed is:

1. A process for the preparation of a compound of formula (I):

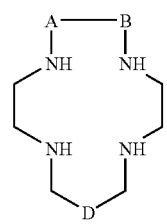

wherein:
one of the groups A and B represents a -(CH$_2$)- radical and the other of the groups A and B represents either a -CH(R')-CH$_2$- radical or a -CH(R")- radical;
in which each of R' and R" is selected from the group consisting of a saturated or unsaturated aliphatic radical comprising from 1 to 12 carbon atoms; a -(CH$_2$)$_n$-O-R$_1$' radical in which n represents an integer between 0 and 4 and R$_1$' represents a hydrogen atom or a saturated or unsaturated aliphatic radical comprising from 1 to 8 carbon atoms; a -(CH$_2$)$_n$-C(=O)-O-R$_1$' radical in which n and R$_1$' are as defined above; and a -(CH$_2$)$_n$-R$_2$' radical in which n is as defined above and in which R$_2$' represents an unsubstituted phenyl radical or a phenyl radical substituted by one or more radicals selected from amino, nitro, chloro, bromo, iodo, methoxy and hydroxyl;
and the group D represents a -(CH$_2$)$_m$- radical in which m is equal to 0 or to 1;
comprising the following successive reaction stages:
a stage (a) during which the compound of formula (II):

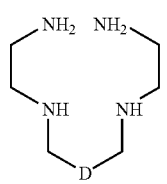

wherein the group D is as defined above, reacts with a compound of formula (III):

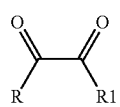

wherein R and R1, which are identical or different, represent, independently of one another, a hydrogen atom or a radical selected from the group consisting of methyl, ethyl, linear propyl, branched propyl, linear butyl and branched butyl to form a compound of formula (IV):

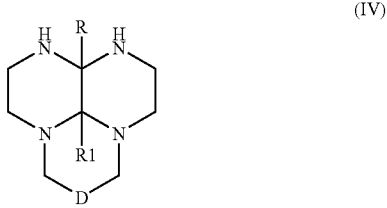

wherein D, R and R1 are as defined above;
a stage (b) during which the compound of formula (IV) obtained in stage (a) reacts with the compound of formula (V):

wherein A and B are as defined above and X represents a radical selected from bromo, iodo, chloro and tosylate, to form the compound of formula (VI):

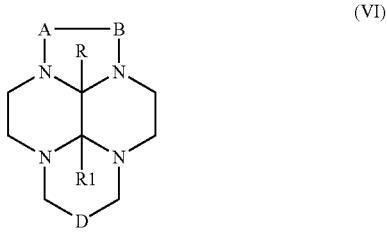

wherein A, B, D, R and R1 are as defined above; and
a stage (c) during which the compound of formula (VI) obtained in stage (b) is subjected to an acid treatment, to form said compound of formula (I).

2. The process according to claim 1, wherein R and R1 are each independently selected from the group consisting of hydrogen and methyl.

3. A compound of formula (Ia):

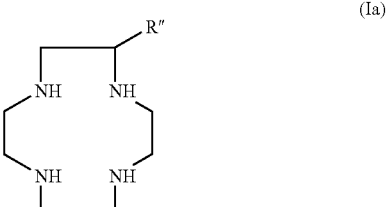

wherein R" is selected from the group consisting of
a -(CH$_2$)$_n$—O—R$_1$' radical in which n represents an integer between 0 and 4 and R$_1$' represents a hydrogen atom or a saturated or unsaturated aliphatic radical comprising from 1 to 8 carbon atoms;

a -$(CH_2)_n$—C (=O)—O—$R_1'$ radical in which n and $R_1'$ are as defined above; and a -$(CH_2)_n$-$R_2'$ radical in which n is as defined above and $R_2'$ represents an unsubstituted phenyl radical or a phenyl radical substituted by one or more radicals selected from the group consisting of amino, nitro, chloro, bromo, iodo, methoxy and hydroxyl, and wherein R" does not represent hydroxymethyl.

* * * * *